United States Patent
Teshima

(10) Patent No.: US 11,058,674 B2
(45) Date of Patent: Jul. 13, 2021

(54) DRUG FOR TREATING COCAINE ADDICTION OR PREVENTING RECURRENCE OF SAME

(71) Applicant: MITSUBISHI TANABE PHARMA CORPORATION, Osaka (JP)

(72) Inventor: Koji Teshima, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 140 days.

(21) Appl. No.: 16/464,178

(22) PCT Filed: Nov. 27, 2017

(86) PCT No.: PCT/JP2017/042425
§ 371 (c)(1),
(2) Date: May 24, 2019

(87) PCT Pub. No.: WO2018/097291
PCT Pub. Date: May 31, 2018

(65) Prior Publication Data
US 2020/0289492 A1      Sep. 17, 2020

Related U.S. Application Data

(60) Provisional application No. 62/426,748, filed on Nov. 28, 2016.

(51) Int. Cl.
   *A61K 31/454*        (2006.01)
(52) U.S. Cl.
   CPC .................................. *A61K 31/454* (2013.01)
(58) Field of Classification Search
   CPC .......................... C07D 401/04; A61K 31/454
   See application file for complete search history.

(56) References Cited

U.S. PATENT DOCUMENTS

| 6,423,725 B1 * | 7/2002 | Ito ........................ C07D 401/04 514/318 |
| 8,877,779 B2 * | 11/2014 | Nakano ................... A61P 25/22 514/322 |
| 2010/0120841 A1 | 5/2010 | Nakano et al. |

FOREIGN PATENT DOCUMENTS

WO      WO 2008/105497 A1      9/2008

OTHER PUBLICATIONS

Extended European Search Report dated Jul. 1, 2020, for European Application No. 17873747.4.
Lutfy et al., "The Nociceptin Receptor as an Emerging Molecular Target for Cocaine Addiction", Progress in Molecular Biology and Translational Science, vol. 137, 2015, pp. 149-181.
Bunzow et al., "Molecular Cloning and Tissue Distribution of a Putative Member of the Rat Opioid Receptor Gene Family that is Not a μ, δ or k Opioid Receptor Type," FEBS Letters, vol. 347, 1994, pp. 284-288.
Ciccocioppo et al., "Attenuation of Ethanol Self-administration and of Conditioned Reinstatement of Alcohol-seeking Behaviour by the Antiopioid Peptide Nociceptin/orphanin FQ in Alcohol-preferring Rats," Psychopharmacology, vol. 172, 2004 (Published online Nov. 18, 2003), pp. 170-178 (10 pages).
Ciccocioppo et al., "Chronic Treatment with Novel Brain-Penetrating Selective NOP Receptor Agonist MT-7716 Reduces Alcohol Drinking and Seeking in the Rat," Neuropsychopharmacology, vol. 39, 2014 (accepted article preview online May 27, 2014), pp. 2601-2610 (11 total pages).
De Guglielmo et al., "MT-7716, A Potent NOP Receptor Agonist, Preferentially Reduces Ethanol Seeking and Reinforcement in Post-dependent Rats," Addiction Biology, vol. 20, 2014, pp. 643-651 (10 total pages).
International Preliminary Report on Patentability and English translation of the Written Opinion of the International Searching Authority, dated May 28, 2019, for International Application No. PCT/JP2017/042425.
International Search Report, dated Jan. 23, 2018, for International Application No. PCT/JP2017/042425, with English translation.
Katz et al., "A Rapid and Inexpensive Technique for Assessing the Reinforcing Effects of Opiate Drugs," Pharmacology Biochemistry & Behavior, vol. 11, 1979, pp. 231-233.
Khroyan et al., "AT-202, A Nociceptin Receptor Agonist, Blocks Drug- and Stress-induced Reinstatement of Extinguished Cocaine Conditioned Place Preference," Neuroscience 2013, Nov. 13, 2013, pp. 1-2.
Kotlińska et al., "Orphanin FQ/nociceptin But Not Ro 65/6570 Inhibits the Expression of Cocaine-induced Conditioned Place Preference," Behavioural Pharmacology, vol. 13, No. 3, 2002, pp. 229-235.
Kuzmin et al., "Acquisition, Expression, and Reinstatement of Ethanol-Induced Conditioned Place Preference in Mice: Effects of Opioid Receptor-Like 1 Receptor Agonists and Naloxone," The Journal of Pharmacology and Experimental Therapeutics, vol. 304, No. 1, 2003, pp. 310-318.
Kuzmin et al., "The Nociceptin/Orphanin FQ Receptor Agonist Ro 64/6198 Reduces Alcohol Self-Administration and Prevents Relapse-Like Alcohol Drinking," Neuropsychopharmacology, vol. 32, 2007 (Published online Jul. 26, 2006), pp. 902-910 (10 total pages).
Martin-Fardon et al., "Nociceptin Prevents Stress-induced Ethanol- But not Cocaine-seeking Behavior in Rats," Neuropharmacology, vol. 11, No. 9, Jun. 26, 2000, pp. 1939-1943.
Meunier et al., "Isolation and Structure of the Endogenous Agonist of Opioid Receptor-like ORL₁ Receptor," Nature, vol. 377, Oct. 12, 1995, pp. 532-535 (5 total pages).

(Continued)

*Primary Examiner* — Kamal A Saeed
(74) *Attorney, Agent, or Firm* — Birch, Stewart, Kolasch & Birch, LLP

(57) ABSTRACT

The present invention provides a drug for treating cocaine addiction or preventing the relapse of the same. Specifically, the present invention provides a drug for treating cocaine addiction or preventing the relapse of the same containing (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof.

8 Claims, 3 Drawing Sheets

(56) References Cited

OTHER PUBLICATIONS

Mogil et al., "The Molecular and Behavioral Pharmacology of the Orphanin FQ/Nociceptin Peptide and Receptor Family," Pharmacological Reviews, vol. 53, No. 3, 2001, pp. 381-415.

Mollereau et al., "ORL1, A Novel Member of the Opioid Receptor Family Cloning, Functional Expression and Localization," FEBS Letters, vol. 341 1994, pp. 33-38.

Neal JR. et al. "Localization of Orphanin FQ (Nociceptin) Peptide and Messenger RNA in the Central Nervous System of the Rat," The Journal of Comparative Neurology, vol. 406, 1999, pp. 503-547.

Neal JR. et al., "Opioid Receptor-Like (ORL1) Receptor Distribution in the Rat Central Nervous System: Comparison of ORL1 Receptor mRNA Expression with $^{125}$I-[$^{14}$Tyr]Orphanin FQ Binding," The Journal of Comparative Neurology, vol. 412, 1999, pp. 563-605.

Reinscheid et al., "Orphanin FQ: A Neuropeptide that Activates an Opioidlike G Protein-Coupled Receptor," Science, vol. 270, Nov. 3, 1995, pp. 792-794 (4 total pages).

Rutten et al., "Effects of the NOP Receptor Agonist Ro65-6570 on the Acquisition of Opiate- and Psychostimulant-induced Conditioned Place Preference in Rats," European Journal of Pharmacology, vol. 645, 2010 (Available online Jul. 30, 2010, pp. 119-126.

Sakoori et al., "Central Administration of Nociceptin/orphanin FQ Blocks the Acquisition of Conditioned Place Preference to Morphine and Cocaine, But not Conditioned Place Aversion to Naloxone . . . ," Psychopharmacology, vol. 172, 2004 (Published online Nov. 18, 2003, pp. 129-136.

Shoblock et al., "The Effect of a Systemically Active ORL-1 Agonist, Ro 64-6198, on the Acquisition, Expression, Extinction, and Reinstatement of Morphine Conditioned Place Preference," Neuropharmacology, vol. 49, 2005, pp. 436-446.

Sukhtankar et al., "Effects of the NOP Agonist SCH221510 on Producing and Attenuating Reinforcing Effects as Measured by Drug Self-administration in Rats," European Journal of Pharmacology, vol. 745, 2014 (Available online Oct. 29, 2014), pp. 182-189.

Woodcock et al., "The Efficacy of a NOP1 Agonist (SCH486757) in Subacute Cough," Lung, vol. 188(Suppl 1), 2010, pp. S47-S52.

Zaveri, "Nociceptin Opioid Receptor (NOP) as a Therapeutic Target: Progress in Translation from Preclinical Research to Clinical Utility," The Journal of Medicinal Chemistry, vol. 59, 2016 (Published Feb. 15, 2016), pp. 7011-7028.

\* cited by examiner

DRUG FOR TREATING COCAINE ADDICTION OR PREVENTING RECURRENCE OF SAME

TECHNICAL FIELD

The present invention relates to a drug for treating cocaine addiction or preventing the relapse of the same comprising an NOP receptor agonist as an active ingredient.

BACKGROUND ART

According to statistics in the United States, the lifetime prevalence of cocaine abuse among adults of 12 years of age or older is 14.5% (https://www.drugabuse.gov/drugs-abuse/cocaine) in 2014. Thus, cocaine abuse is a serious social problem. However, there is no approved drug for effectively treating cocaine abuse, and there is a need for developing a new drug for cocaine abuse.

Meanwhile, NOP receptor is known as one of opioid receptors. The NOP (nociceptin orphanin FQ peptide) receptor also known as ORL1 (opioid receptor-like 1) receptor (see Nonpatent Document 1 and Nonpatent Document 2) is a receptor discovered in 1994 as the fourth opioid receptor behind DOP ($\delta$), KOP($\kappa$), and MOP($\mu$) receptors. The NOP receptor has about 60% amino acid sequence homology with the other opioid receptors. However, the NOP receptor is clearly different from the other opioid receptors in that it does not bind to naloxone which is a nonselective opioid receptor antagonist (see Nonpatent Document 2).

Endogenous ligands of the NOP receptor were successively identified by French and Swiss research groups in 1995, and named nociceptin (see Nonpatent Document 3) and orphanin FQ (see Nonpatent Document 4), respectively (hereinafter also referred to as N/OFQ). The N/OFQ and NOP receptors are widely distributed in central nervous system (see Nonpatent Document 5 and Nonpatent Document 6), and involved in many physiological actions such as pain, learning and memory, feeding, and reward (see Nonpatent Document 7).

Self-administration method and conditioned place preference (CPP) method (see Nonpatent Document 8) are known as methods for evaluating the strength of drug addiction. To date, the self-administration method and CPP method have shown that the N/OFQ or low-molecular NOP receptor agonists suppress the reinforcing effects of alcohol (see Nonpatent Document 9, Nonpatent Document 10, Nonpatent Document 11, Nonpatent Document 12, and Nonpatent Document 13) and opioid (see Nonpatent Document 14, Nonpatent Document 15, and Nonpatent Document 17), namely the desire to repeatedly take a drug (also referred to as "rewarding effects").

Meanwhile, few reports have suggested the effectiveness of NOP receptor agonists against cocaine addiction, and especially the effectiveness of low-molecular NOP receptor agonists has not been confirmed (see Nonpatent Document 16, Nonpatent Document 17, Nonpatent Document 18, Nonpatent Document 19, and Nonpatent Document 20).

Also, a molecule with high selectivity of the NOP receptor relative to the MOP receptor is desirable as an NOP receptor agonist to be used in treating cocaine addiction or preventing the relapse of the same. However, SCH221510 (see Nonpatent Document 21), which is a compound having the highest selectivity of the NOP receptor relative to the MOP receptor among low-molecular NOP receptor agonists reported to date, suppresses the opioid self-administration in rat by intracerebral administration, but does not suppress it by peripheral (subcutaneous) administration (see Nonpatent Document 14). Thus, it is believed that said compound shows low migration to brain (see Nonpatent Document 21), and is not sufficiently effective as an NOP receptor agonist against a cocaine addiction model. Accordingly, it is desired to develop a compound which is a low-molecular NOP receptor agonist having high receptor selectivity and showing high migration to brain, as well as effective at a low dose not producing side effects such as sleepiness caused by a central nervous system (CNS) depressant action of the NOP receptor agonist (Nonpatent Document 22). However, a low-molecular compound showing effectiveness in a cocaine addiction model with high clinical predictability such as a cocaine self-administration model in primate has not been reported to date (see Nonpatent Document 21).

Other low-molecular NOP receptor agonists such as a benzimidazole compound are known (see Patent Document 1). However, effectiveness of said compound against cocaine addiction is not specifically disclosed.

CITATION LIST

Patent Document

Patent Document 1: WO 2008/105497 pamphlet

Nonpatent Document

Nonpatent Document 1: FEBS Lett. 347:284-288, 1994.
Nonpatent Document 2: FEBS Lett. 341:33-38, 1994.
Nonpatent Document 3: Nature 377:532-535, 1995.
Nonpatent Document 4: Science 270:792-794, 1995.
Nonpatent Document 5: J. Comp. Neurol. 412:563-605, 1999.
Nonpatent Document 6: J. Comp. Neurol. 406:503-547, 1999.
Nonpatent Document 7: Pharmacol. Rev. 53:381-415, 2001.
Nonpatent Document 8: Pharmacol. Biochem. Behav. 11:231-233, 1979.
Nonpatent Document 9: Psychopharmacology 172:170-178, 2004.
Nonpatent Document 10: Neuropsychopharmacology 32:902-910, 2007.
Nonpatent Document 11: Addict. Biol. 20:643-651, 2015.
Nonpatent Document 12: Neuropsychopharmacology 39, 2601-2610, 2014.
Nonpatent Document 13: J. Phramacol. Exp. Ther. 304:310-318, 2003.
Nonpatent Document 14: Eur. J. Pharmacol. 745:182-189, 2014.
Nonpatent Document 15: Neuropharmacology 49, 439-446, 2005.
Nonpatent Document 16: NeuroReport 11:1939-1943, 2000.
Nonpatent Document 17: Psychopharmacology 172:129-136, 2004.
Nonpatent Document 18: Behav. Pharmacol. 13:229-235, 2002.
Nonpatent Document 19: Eur. J. Pharmacol. 645:119-126, 2010.
Nonpatent Document 20: Society for Neuroscience, 2013. Program No. 733.24
Nonpatent Document 21: J. Med. Chem. 59:7011-7028, 2016.
Nonpatent Document 22: Lung 188:S47-S52, 2010.

SUMMARY OF THE INVENTION

Problems to be Solved by Invention

The present inventor has earnestly studied to find a compound which is a low-molecular NOP receptor agonist having high selectivity of the NOP receptor and showing high migration to brain, as well as showing effectiveness at a low dose not producing side effects such as sleepiness, evaluated the effectiveness of an NOP receptor agonist having the following structure, i.e., (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide (hereinafter also referred to as "Compound A") or a pharmaceutically acceptable salt thereof in monkey and rat cocaine addiction models, as a result thereof found that the Compound A or a pharmaceutically acceptable salt thereof has effects for treating cocaine addiction and effects for preventing the relapse of cocaine addiction, and finally completed the present invention.

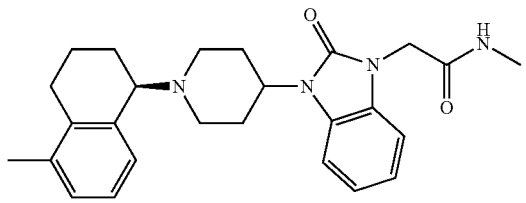

Means to Solve Problems

Namely, the present invention includes the followings.
(1) A pharmaceutical composition for treating cocaine addiction or preventing the relapse of cocaine addiction comprising (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof.
(2) A method for treating cocaine addiction comprising administering (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof to a patient in need of treatment.
(3) The method for treating cocaine addiction according to the above (2), wherein the daily dose of (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof is 0.01 to 30 mg.
(4) A method for preventing the relapse of cocaine addiction comprising administering (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof to a patient in need of treatment.
(5) The method for preventing the relapse of cocaine addiction according to the above (4), wherein the daily dose of (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof is 0.01 to 30 mg.
(6) The pharmaceutical composition according to the above (1), wherein the cocaine addiction is a disease selected from the group consisting of cocaine abuse, psychiatric symptoms and physical symptoms caused by cocaine use, and re-intake (relapse).
(7) The method for treating cocaine addiction according to the above (2) or (3), wherein the cocaine addiction is a disease selected from the group consisting of cocaine abuse, psychiatric symptoms and physical symptoms caused by cocaine use, and re-intake (relapse).
(8) The method for preventing the relapse of cocaine addiction according to the above (4) or (5), wherein the cocaine addiction is a disease selected from the group consisting of cocaine abuse, psychiatric symptoms and physical symptoms caused by cocaine use, and re-intake (relapse).
(9) The pharmaceutical composition according to the above (1) or (6), or the method for treating cocaine addiction or the method for preventing the relapse of cocaine addiction according to any one of the above (2) to (5) or (7) to (8), wherein the cocaine addiction is a withdrawal symptom after withdrawal of cocaine.
(10) Use of (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof for the manufacture of a pharmaceutical composition for treating cocaine addiction or preventing the relapse of cocaine addiction.
(11) Use of (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof for treating cocaine addiction or preventing the relapse of cocaine addiction.
(12) The use according to the above (10) or (11), wherein the cocaine addiction is a disease selected from the group consisting of cocaine abuse, psychiatric symptoms and physical symptoms caused by cocaine use, and re-intake (relapse).
(13) (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof for treating cocaine addiction or preventing the relapse of cocaine addiction.
(14) (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof for treating cocaine addiction or preventing the relapse of cocaine addiction according to the above (13), wherein the cocaine addiction is a disease selected from the group consisting of cocaine abuse, psychiatric symptoms and physical symptoms caused by cocaine use, and re-intake (relapse).
(15) The use according to any one of the above (10) to (12), or (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof for treating cocaine addiction or preventing the relapse of cocaine addiction according to the above (13) or (14), wherein the cocaine addiction is a withdrawal symptom after withdrawal of cocaine.

Effect of Invention

The Compound A or a pharmaceutically acceptable salt thereof which is an active ingredient of the present invention may be used as a drug effective for treating cocaine addiction or preventing the relapse of the same. Also, the Compound A or a pharmaceutically acceptable salt thereof may be used as a drug for treating cocaine abuse, psychiatric symptoms and physical symptoms caused by cocaine use (for example, a withdrawal symptom after withdrawal of cocaine), and re-intake (relapse), or preventing the relapse of the same.

MODE FOR CARRYING OUT THE INVENTION

Figure 1:
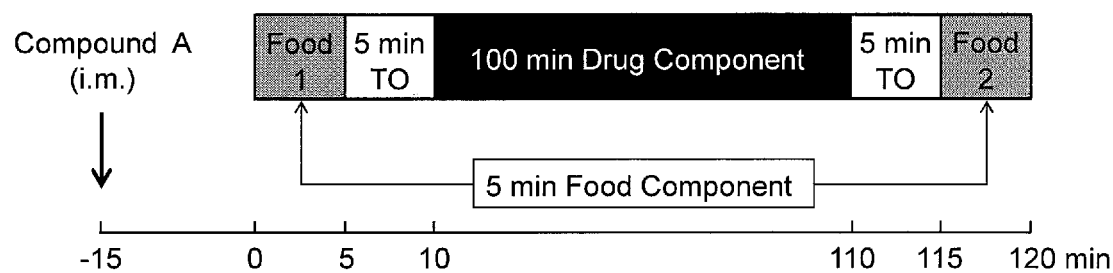
FIG. 1 A figure showing a test protocol of a cocaine self-administration in monkey. In the protocol, a 100 minutes cocaine self-administration test (100 min Drug Component), 5 minutes time-out periods (5 min TO; periods during which any reward cannot be acquired by a lever press) before and after the 100 min Drug Component, and 5 minutes food acquisition tests (5 min Food Component (Food 1, Food 2)) before and after the 5 min TO in order to evaluate the effect of the Compound A on the lever press behavior itself were carried out. The horizontal axis shows the time course after the intramuscular administration of the Compound A (Compound A (i.m.)).

Hereinafter, the present invention is described more in detail.

The Compound A of the present invention may be prepared according to the method described in Example 10 of the Patent Document 1.

The Compound A or a pharmaceutically acceptable salt thereof of the present invention encompasses compounds labeled with an isotope (for example, $^{2}H$, $^{3}H$, $^{13}C$, $^{14}C$, $^{15}N$, $^{18}F$, $^{32}P$, $^{35}S$, and $^{125}I$) and the like, and deuterated products thereof.

Examples of the pharmaceutically acceptable salt of the Compound A of the present invention include acid addition salts with inorganic acids and organic acids or salts with inorganic bases. Specific examples thereof include acid addition salts with inorganic acids and organic acids such as hydrochloric acid, oxalic acid, maleic acid, and fumaric acid, and salts with inorganic bases such as sodium, potassium, calcium, and magnesium.

Also, the present invention includes a racemic mixture of the Compound A or the corresponding enantiomers thereof.

The term of "patient" in the present description refers to an individual to be subjected to the treatment or relapse prevention by the Compound A or a pharmaceutically acceptable salt thereof, and preferably a human.

The term of "cocaine addiction" in the present description is used in a broad concept to include cocaine abuse, psychiatric symptoms and physical symptoms caused by cocaine use (for example, a withdrawal symptom after withdrawal of cocaine), and re-intake (relapse). Also, examples of the symptoms included in the term of "psychiatric symptoms" in the present description include, but are not limited to, weakness, loss of appetite, anxiety, depression, and a withdrawal symptom after withdrawal of cocaine. Further, examples of the symptoms included in the term of "physical symptoms" in the present description include, but are not limited to, pupillary dilatation, blood pressure elevation, convulsion, sleep disorder, extreme neurosis, hallucination, delusion, and a withdrawal symptom after withdrawal of cocaine.

Also, the present invention not only may treat cocaine addiction, but also may prevent the relapse due to a craving for cocaine caused by various stresses after withdrawal of cocaine. In this regard, examples of the stresses include, but are not limited to, psychological stresses (for example, loneliness, anxiety feeling, alienation, fatigue, and harassment) and physical stresses (for example, noise, illness, pain, injury, lack of sleep, and overwork).

A medicine comprising the Compound A or a pharmaceutically acceptable salt thereof of the present invention as an active ingredient may be orally or parenterally administered. Examples of the dosage form include a tablet, a capsule, a granule, a powder, an injection, an oral tablet, a liniment, an ointment, and a suppository. They may be formulated by using a widely used technique with a pharmaceutically acceptable carrier if necessary. The pharmaceutically acceptable carrier may be a conventional carrier in this technical field, and examples thereof include bulking agents (for example, lactose, sucrose, cornstarch, potassium phosphate, sorbit, glycine, mannitol, and crystalline cellulose), lubricants (for example, magnesium stearate, talc, polyethylene glycol, and silica), binders (for example, syrup, gum arabic, gelatin, sorbit, tragacanth, polyvinylpyrrolidone, hydroxypropylcellulose, polyvinyl alcohol, and polyethylene glycol), disintegrants (for example, potato starch, low substituted hydroxypropylcellulose, and cross-linked carboxymethyl cellulose), coating agents or film-forming agents (for example, ethyl cellulose and hydroxypropyl methylcellulose), and ointment bases (for example, vaseline and paraffin). For example, when the medicine of the present invention is an oral agent such as a tablet, a capsule, a granule, and a powder, a bulking agent, a lubricant, a binder, a disintegrant, a coating agent, a film-forming agents, or the like may be used if necessary to prepare the medicine. When the medicine of the present invention is an ointment, a widely used base may be used to prepare the medicine. The Compound A of the present invention is confirmed to show high migration to brain, and thus especially suitable as an oral agent.

The dose (i.e., effective amount) of the Compound A or a pharmaceutically acceptable salt thereof which is an active ingredient of the present invention may be appropriately determined depending on symptoms, age and body weight of a patient, the dosage form, and the like. When it is formulated into an oral agent, it may be usually administered at a dose of 0.01 to 30 mg, preferably 0.1 to 3 mg per day at once or in divided doses. Also, it is known that an NOP receptor agonist would produce side effects such as sleepiness based on a central nervous system (CNS) depressant action caused by the characteristics of the action mechanism (Nonpatent Document 22), and thus it is very important to determine an appropriate dose in order to use it safely and effectively. Namely, it is desirable to administer it at a dose of one third to one-thirtieth of the dose at which a central nervous system (CNS) depressant action is observed in an experimental animal. Also, it is desirable to use a primate as an experimental animal in evaluating a central nervous system (CNS) depressant action in view of the ease of extrapolating the dose to human, and a test protocol in which a main effect and a central nervous system (CNS) depressant action can be simultaneously evaluated in the same individual is desirable. In view of the results in Example 1 and a pharmacokinetic test of monkey, the dose of the Compound A in human may be estimated to be 0.1 to 3 mg, and the Compound A is believed to be preferably used within a range of said dose.

Next, the method for evaluating the cocaine addiction is described.

The strength of drug addiction may be investigated by using the reinforcing effects (rewarding effects) as an index, and examples of the methods for non-clinically measuring the reinforcing effects include the self-administration method. In the self-administration method, the strength of addiction may be investigated by using the lever press behavior as an index under the conditions wherein a drug is automatically intravenously administered from an infusion pump when a lever is pressed. The self-administration method is the most reliable method for evaluating the reinforcing effects of a drug, but has a disadvantage that it requires a long period of time for the training of self-administration. The conditioned place preference (CPP) method was developed as a method for overcoming said disadvantage and evaluating the drug addiction within a relatively short period of time (see Nonpatent Document 8), and widely used as an evaluation system for addiction mainly using a mouse or a rat. However, the CPP method is a method for predicting the reinforcing effects using the place preference as an index, and is not a system for directly evaluating the reinforcing effects. The CPP method may evaluate the effects on the conditioning of place preference caused by an addictive drug, i.e., the effects on the acquisition of CPP, the effects on the expression of CPP after the acquisition of the place preference, and the effects on the relapse (reinstatement) for restoring the place preference caused by a stress load or the like after the extinction of the once acquired place preference. Meanwhile, the self-administration method requires a long period of time for the training and thus does not evaluate an effect on the acquisition, but may evaluate the effects on the drug uptake behavior after the acquisition of the self-administration and the effects on the drug seeking behavior caused by a stress load or the like after the extinction of the self-administration.

To date, the self-administration method and the CPP method have confirmed that the N/OFQ or a low-molecular NOP receptor agonist suppresses the reinforcing effects of alcohol (see Nonpatent Document 9, Nonpatent Document 10, Nonpatent Document 11, Nonpatent Document 12, and Nonpatent Document 13) and opioid (see Nonpatent Document 14, Nonpatent Document 15, and Nonpatent Document 17). The effects of NOP receptor agonists in evaluation systems of alcohol addiction reported to date are summarized in Table 1. The symbols such as "9)" in the table represent the Nonpatent Document numbers in which the results of each experiment are disclosed (the same is true on the Table 2). The effectiveness of the NOP receptor agonists on alcohol addiction is suggested by the results of more than one low-molecular compounds.

Table 1

Summary of effects of NOP receptor agonists in evaluation systems of alcohol addiction

| | Evaluation system | | | | |
| --- | --- | --- | --- | --- | --- |
| | Self-administration | | Conditioned place preference | | |
| Drug name | Uptake behavior | Seeking behavior | Acquisition | Expression | Relapse |
| N/OFQ | o [9] | o [9] | o [13] | o [13] | o [13] |
| Ro64-6198 | o [10] | N.T. | o [13] | o [13] | o [13] |
| MT-7716 | o [11] | o [12] | N.T. | N.T. | N.T. | o: Effective,
N.T.: Not Tested

Ro64-6198: (1S,3aS)-8-(2,3,3a,4,5,6-hexahydro-1H-phenalen-1-yl)-1-phenyl-1,3,8-triaza-spiro[4.5]decan-4-one hydrochloride MT-7716: (R)-2-{3-[1-(acenaphthen-1-yl)piperidin-4-yl]-2-oxo-2,3-dihydro-1H-benzimidazol-1-yl}-N-methylacetamide hydrochloride monohydrate On the other hand, there are only a few reports on effects of NOP receptor agonists on cocaine addiction, and there is only one report on the self-administration method disclosing that the N/OFQ does not suppress the cocaine seeking behavior induced by a stress after the extinction of the cocaine self-administration in rat (see Nonpatent Document 16). In addition to said report, there are the reports on the compounds in the CPP method as shown in the following table.

The intraventricular administration of N/OFQ to a mouse blocks the CPP acquisition (see Nonpatent Document 17) and the CPP expression (see Nonpatent Document 18) caused by cocaine. Meanwhile, Ro65-6570 (see Nonpatent Document 18 and Nonpatent Document 19) which is a low-molecular NOP receptor agonist does not affect the CPP acquisition and the CPP expression caused by cocaine. Also, AT-202 (see Nonpatent Document 20) which is also a low-molecular NOP receptor agonist does not affect the CPP acquisition, but suppresses the relapse of CPP caused by a stress. The reports on the effects of NOP receptor agonists in the above evaluation systems of cocaine addiction are summarized in Table 2.

Table 2 Summary of effects of NOP receptor agonists in evaluation systems of cocaine addiction Summary of effects of NOP receptor agonists in evaluation systems of cocaine addiction

| | Evaluation system | | | | |
|---|---|---|---|---|---|
| | Self-administration | | Conditioned place preference | | |
| Drug name | Uptake behavior | Seeking behavior | Acquisition | Expression | Relapse |
| N/OFQ | N.T. | x [16] | o [17] | o [18] | N.T. |
| Ro65-6570 | N.T. | N.T. | x [19] | x [18] | N.T. |
| AT-202 | N.T. | N.T. | x [20] | N.T. | o [20] | o: Effective,
x: Ineffective,
N.T.: Not Tested

Ro65-6570: 8-acenaphthen-1-yl-phenyl-1,3,8-triaza-spiro[4.5]decan-4-one hydrochloride
AT-202: 1-[1-(2,3,3a,4,5,6-hexahydro-1H-phenalen-1-yl)piperidin-4-yl]-indolin-2-one In this regard, it is likely that the low-molecular NOP receptor agonists reported to date may have insufficient receptor selectivity, and thus these compounds were not effective in the evaluation system in which the endogenous agonist N/OFQ was effective (CPP Acquisition and CPP Expression). Namely, it is likely that both compounds of Ro65-6570 and AT-202 may have agonist activities not only on the NOP receptor, but also on the MOP receptor, and thus the NOP receptor agonist activity was insufficiently differentiated. Accordingly, it is likely that the effects caused by the NOP receptor agonist activity was reduced or disappeared by the expression of addiction based on the MOP receptor agonist activity. Also, SCH221510 is the compound which has the highest selectivity of the NOP receptor relative to the MOP receptor among the low-molecular NOP receptor agonists reported to date (see Nonpatent Document 21). However, it is believed that SCH221510 shows low migration to brain (see Nonpatent Document 21), because it suppresses the opioid self-administration in rat by the intracerebral administration, but does not suppress the same by the peripheral (subcutaneous) administration (see Nonpatent Document 14).

Also, examples of the addictive substances include central depressants such as alcohol and morphine; and psychostimulants (central stimulants) such as cocaine and methamphetamine. However, it is believed that the pathological mechanisms of addiction caused by both drugs are different with each other, and a drug effective for alcohol or morphine addiction is not necessarily also effective for cocaine addiction. In order to demonstrate this matter, it is necessary to use and evaluate a low-molecular NOP receptor agonist which has high receptor selectivity and shows high migration to brain in a cocaine addiction model with high clinical predictability.

The Compound A or a pharmaceutically acceptable salt thereof of the present invention has high affinity to the NOP receptor and low affinity to the MOP receptor. Accordingly, it has high NOP receptor selectivity, shows high migration to brain, and is highly effective even at a low dose which does not cause a central nervous system (CNS) depressant action of the NOP receptor agonist.

EXAMPLES

Hereinafter, the present invention is specifically illustrated by means of Examples, but is not limited to the range described in these Examples. The following experiments were carried out according to the method disclosed in Psychopharmacology 160:362-370, 2002.

Example 1: Effects of Compound a on Cocaine Self-Administration in Monkey and Central Nervous System (CNS) Depressant Action (Method)
Four rhesus monkeys were used in the experiment. Each monkey was put in a stainless steel chamber (64×64×79 cm), and a training was carried out under the condition that the monkey received a 1 g of food pellet with banana flavor as a reward when the monkey touched a reaction key on an operant panel (28×28 cm) placed on the wall in front of the chamber. After the training was carried out until the monkey stably acquired the reward under the condition of FR30 (one food reward could be obtained by thirty touches of the reaction key), the monkey was operated to indwell a catheter for cocaine administration into a vein. After the monkey recovered from the operation, a training was carried out under the condition that cocaine was intravenously injected as a reward by touching the reaction key on the operant panel to prepare a cocaine self-administration model.

The Compound A was evaluated by the experiment protocol shown in FIG. 1. Namely, after the Compound A or saline as a control was intramuscularly administered 15 minutes before the start, a 120 minutes session was carried out. The 120 minutes session consisted of the 100 minutes drug component during which cocaine was intravenously injected as a reward by touching the reaction key on the operant panel (100 min Drug Component), the 5 minutes time-out components during which any reward could not be obtained by touching the reaction key on the operant panel (5 min TO) before and after the 100 min Drug Component, and the first 5 minutes and last 5 minutes food components during which food rewards could be obtained by touching the reaction key on the operant panel (5 min Food Component (Food 1, Food 2)). A red LED lamp in the reaction key was turned on during the food components, a green LED lamp in the reaction key was turned on during the drug component, and a yellow LED lamp in the reaction key was turned on during the time-out components. Further, the condition under which a next reward could not be obtained until a certain period of time elapsed after a reward was obtained, i.e., a time-out period was set during each period of the food components and the drug component. The time-out period was 10 seconds for the food components and 60 seconds for the drug component, and a yellow LED lamp in the reaction key was turned on during the time-out periods. The tests of the food components and the drug component were carried out under the condition of FR30.
(Results)

Figure 2:
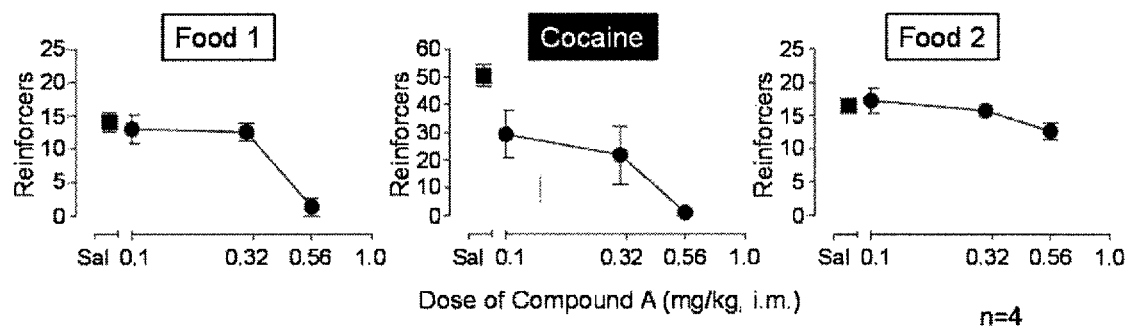
FIG. 2 Figures showing the results of studies of the effects of the Compound A on the cocaine self-administration in monkey under the conditions using various doses of Compound A. The left figure shows the results of food acquisition test (Food 1) before the cocaine self-administration test, the central figure shows the results of the cocaine self-administration test (Cocaine), and the right figure shows the results of the food acquisition test (Food 2) after the cocaine self-administration test, respectively. In each figure, the vertical axis shows the number of acquired rewards (cocaine self-injection or food pellet) (Reinforcers), the horizontal axis shows the dose of Compound A (Dose of Compound A (mg/kg, i.m.)), and the Sal shows the saline administration group as a control. The Compound A decreased the number of cocaine rewards at a dose which did not affect the number of food acquisition.

As the results, the Compound A dose-dependently reduced the number of rewards in the cocaine self-administration at doses of 0.1, 0.32, and 0.56 mg/kg as shown in the central figure of FIG. 2. Also, the Compound A reduced the number of food acquisition at the dose of 0.56 mg/kg in the food component 1 (Food 1), which suggests that the dose of 0.56 mg/kg was a dose causing a central nervous system (CNS) depressant action. Meanwhile, the Compound A was proved to suppress the cocaine self-administration even at doses (0.1 and 0.32 mg/kg) which did not affect the number of food acquisition in the food component 1 (Food 1). Namely, it was proved that the Compound A was effective as a drug for treating cocaine addiction even at a low dose which did not cause a central nervous system (CNS) depressant action. Further, the reduction of the number of food acquisition caused by the Compound A at a dose of 0.56 mg/kg in the food component 1 (Food 1) was not observed in the food component 2 (Food 2), which suggests that the central nervous system (CNS) depressant action of the Compound A was a transient action.

Example 2: Effects of Compound a on Cocaine Self-Administration in Monkey at Various Doses of Cocaine (Method)

The effects of the Compound A on the cocaine self-administration were investigated under the conditions using various doses (0.001 to 0.1 mg/kg/injection) of cocaine according to the same method as the Example 1. The Compound A was used at doses which did not affect the number of the food acquisition in the food component 1 (Food 1) in Example 1, i.e., at a dose of 0.1 mg/kg (one example) or 0.32 mg/kg (three examples).
(Results)

Figure 3:
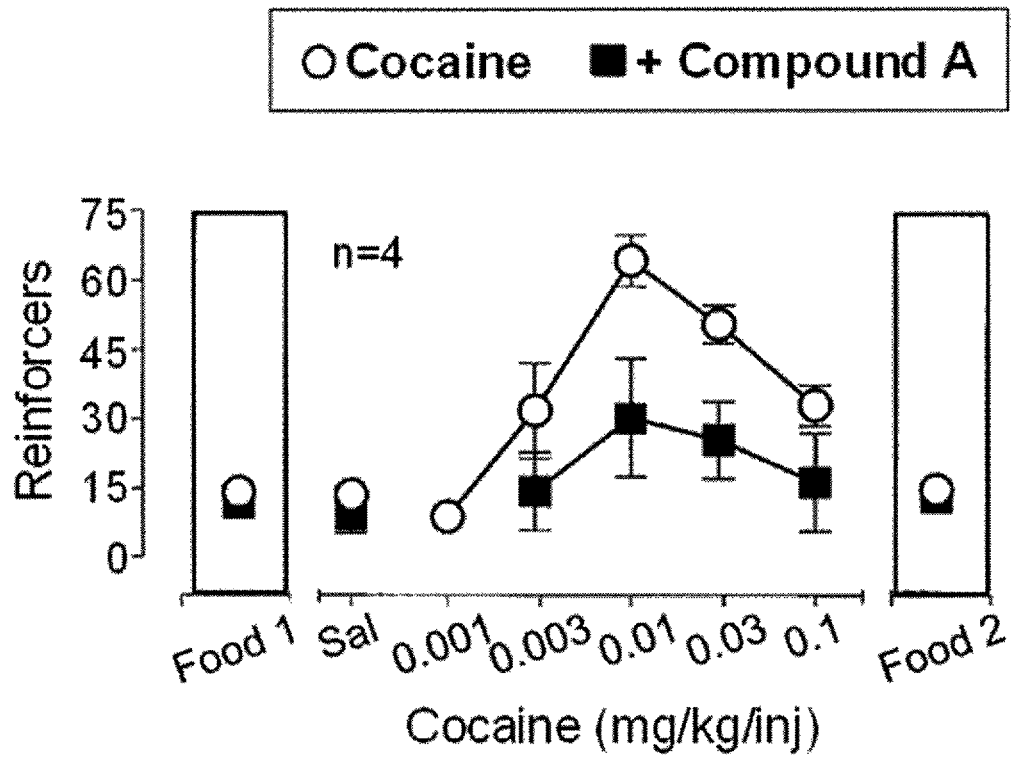
FIG. 3 A figure showing the results of studies of the effects of the Compound A on the cocaine self-administration in monkey under the conditions using various doses of cocaine. The vertical axis shows the number of acquired rewards (cocaine self-injection or food pellet), and the horizontal axis shows the dose of cocaine per injection. The Compound A was used at a dose of 0.1 or 0.32 mg/kg which did not cause a central nervous system (CNS) depressant action in view of the results in FIG. 2. The Sal shows the saline administration group as a control. While the relationship between the dose of cocaine and the number of rewards showed a bell-shape response, the Compound A significantly decreased the number of rewards at the condition which showed the strongest rewarding effects of cocaine (at the condition of cocaine dose of 0.01 mg/kg/inj).

As the results, the average data of the four examples showed that the administration of the Compound A significantly reduced the number of rewards of the cocaine self-administration at the cocaine doses of 0.003, 0.01, 0.03, and 0.1 mg/kg/injection as shown in FIG. 3.

Also, patients with cocaine addiction can find by themselves a cocaine dose at which the sufficient reinforcing effects can be obtained. Thus, a drug which shifts the dose-response curve of cocaine (the graph of the symbol "o" in FIG. 3) rightward is not effective as a treatment drug. Namely, such a drug would suppress the reinforcing effects at a low dose of cocaine only, but does not suppress the reinforcing effects at a high dose of cocaine, and thus is not sufficient as a treatment drug. Meanwhile, the Compound A significantly suppressed the effects of cocaine at any cocaine doses from low doses to high doses as shown in the graph of the symbol "■" in FIG. 3, and thus was proved to have pharmacological activities as an excellent drug for treating cocaine addiction.

Example 3: Effects of Compound a on Stress-Induced Cocaine

Seeking Behavior in Rat
(Method)

Figure 4:
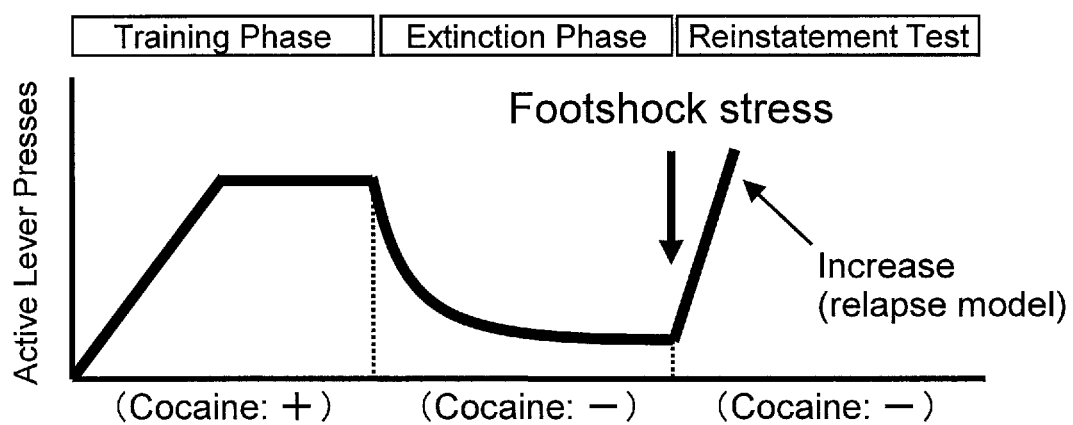
FIG. 4 A figure showing a test protocol of stress-induced cocaine seeking behavior in rat. The vertical axis shows the number of lever presses in relation to rewards (Active Lever Presses), the horizontal axis shows the time from the start of training, and the line graph shows an image of the change of the number of lever presses with time. After the training period during which cocaine rewards can be acquired (Training Phase), a period during which cocaine rewards cannot be acquired (Extinction Phase) is placed, subsequently a Footshock stress is given, and the number of lever presses is measured (Reinstatement Test), then the number of lever presses is increased by the induction of cocaine seeking behavior caused by the Footshock stress (Increase (relapse model)). The effects of the Compound A to prevent the relapse of cocaine addiction induced by a stress can be evaluated by measuring the decrease of the number of lever presses caused by the oral administration (p.o.) of the Compound A.

A group of twelve examples of male Long-Evans hooded rats was used in the experiment. After each rat was operated to indwell a catheter for cocaine administration into an external jugular vein and recovered for a period of five days or more, a cocaine self-administration training was started. A chamber which had two levers on the wall surface and a grid for footshock on the floor was used in the training. Each rat was put in the chamber once a day (2 hours/session), acquired the self-administration under the condition that a cocaine solution (0.2 ml/6 seconds, cocaine 0.5 mg/kg) was intravenously injected when the rat pressed one time (FR1) an active lever (right lever). As shown in FIG. 4, after a stable number of lever presses was observed in the training period (Training Phase), a period during which any cocaine reward could not be obtained by pressing the active lever (Extinction Phase) was placed to erase the lever press behavior. The rat in which the lever press behavior was erased was exposed to a 15 minutes footshock (0.63 mA, 0.5 seconds, intervals of 40 seconds), and then the number of lever presses for 2 hours/session was recorded (Reinstatement Test). The Compound A or a solvent as a control was orally administered 30 minutes before the start of the session of reinstatement test.
(Results)

Figure 5:
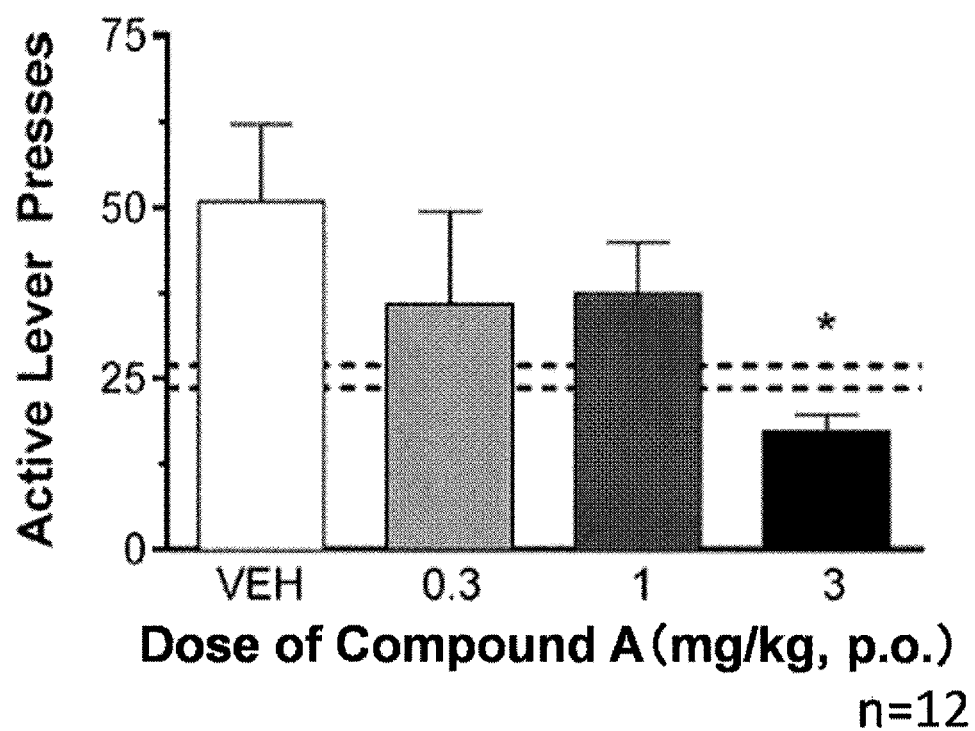
FIG. 5 A figure showing the results of studies of the effects of the Compound A on stress-induced cocaine seeking behavior in rat. The vertical axis shows the number of lever presses in relation to rewards, the horizontal axis shows the dose of Compound A (Dose of Compound A (mg/kg, p.o.)), and the VEH shows the solvent treated group as a control. The dotted line shows the width of average value of the number of lever presses in each group at the final day (the day before the Reinstatement Test) of the extinction process (Extinction Phase). The Compound A significantly suppressed the stress-induced cocaine seeking behavior at a dose of 3 mg/kg (*<0.05 vs solvent treated group).

As the results, the administration of the Compound A at a dose of 3 mg/kg significantly suppressed the cocaine seeking behavior induced by the footshock stress as shown in FIG. 5. The results demonstrate that the Compound A suppresses the desire for taking cocaine caused by a stress, namely has effects to prevent the relapse of cocaine addiction caused by a stress.

The above results demonstrate that the Compound A may be not only a drug for treating cocaine addiction, but also a drug for preventing the relapse of cocaine addiction cause by a stress.

INDUSTRIAL APPLICABILITY

The medicine of the present invention may be used as a drug for treating cocaine addiction or a drug for preventing the relapse of the same.

The invention claimed is:

1. A method for treating cocaine addiction comprising administering (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof to a patient in need of treatment.

2. The method for treating cocaine addiction according to claim 1, wherein the daily dose of (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof is 0.01 to 30 mg.

3. A method for reducing the likelihood of a relapse of cocaine addiction comprising administering (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof to a patient in need of treatment.

4. The method for reducing the likelihood of a relapse of cocaine addiction according to claim 3, wherein the daily dose of (R)-2-{3-[1-(5-methyl-1,2,3,4-tetrahydronaphthalen-1-yl)piperidin-4-yl]-2,3-dihydro-2-oxo-benzimidazol-1-yl}-N-methylacetamide or a pharmaceutically acceptable salt thereof is 0.01 to 30 mg.

5. The method for treating cocaine addiction according to claim 1, wherein the cocaine addiction is a disease selected from the group consisting of cocaine abuse, psychiatric symptoms and physical symptoms caused by cocaine use, and re-intake (relapse).

6. The method for reducing the likelihood of a relapse of cocaine addiction according to claim 3, wherein the cocaine addiction is a disease selected from the group consisting of cocaine abuse, psychiatric symptoms and physical symptoms caused by cocaine use, and re-intake (relapse).

7. The method for treating cocaine addiction according to claim 1, wherein the cocaine addiction is a withdrawal symptom after withdrawal of cocaine.

8. The method for reducing the likelihood of a relapse of cocaine addiction according to claim 3, wherein the cocaine addiction is a withdrawal symptom after withdrawal of cocaine.

* * * * *